United States Patent
Junaedi et al.

(10) Patent No.: US 10,697,915 B1
(45) Date of Patent: Jun. 30, 2020

(54) SENSOR FOR DETERMINING A PHYSICOCHEMICAL PROPERTY OF A LIQUID FUEL

(71) Applicant: PRECISION COMBUSTION, INC., North Haven, CT (US)

(72) Inventors: Christian Junaedi, Cheshire, CT (US); Subir Roychoudhury, Madison, CT (US)

(73) Assignee: PRECISION COMBUSTION, INC., North Haven, CT (US)

( * ) Notice: Subject to any disclaimer, the term of this patent is extended or adjusted under 35 U.S.C. 154(b) by 342 days.

(21) Appl. No.: 15/606,077

(22) Filed: May 26, 2017

Related U.S. Application Data (60) Provisional application No. 62/346,606, filed on Jun. 7, 2016.

(51) Int. Cl.
*G01N 25/28* (2006.01)
*G01N 33/22* (2006.01)

(52) U.S. Cl.
CPC ............. *G01N 25/28* (2013.01); *G01N 33/22* (2013.01)

(58) Field of Classification Search
CPC .............................. G01N 25/28; G01N 33/22
USPC .............................................. 73/35.02, 61.78
See application file for complete search history.

(56) References Cited

U.S. PATENT DOCUMENTS

| | | |
|---|---|---|
| 3,738,808 A | 6/1973 | Cunningham et al. |
| 4,057,393 A | 11/1977 | Budzak et al. |
| 4,397,958 A | 8/1983 | Vroom |
| 4,549,815 A | 10/1985 | Venkat et al. |
| 5,457,985 A | 10/1995 | Cellier et al. |
| 5,906,190 A | 5/1999 | Hole et al. |
| 7,289,900 B2 | 10/2007 | Wilharm et al. |
| 7,421,884 B2 | 9/2008 | Aoyama |
| 7,949,471 B2 | 5/2011 | Ritz |
| 2012/0295365 A1 | 11/2012 | Maruta et al. |
| 2016/0178469 A1 | 6/2016 | Berkhous et al. |

FOREIGN PATENT DOCUMENTS

| | | |
|---|---|---|
| GB | 394736 A | 7/1933 |
| GB | 1340731 A | 12/1973 |

OTHER PUBLICATIONS

Abstract of ASTM-D613, "Standard Test Method for Cetane Number of Diesel Fuel Oil", ASTM International, 2001; as disclosed at "www.MADCAD.com".

(Continued)

*Primary Examiner* — Daniel S Larkin
(74) *Attorney, Agent, or Firm* — Marie F. Zuckerman (57) ABSTRACT

A portable, compact, real-time and accurate sensor and method for deriving a physicochemical property of a liquid fuel, such as cetane number, carbon content, carbon/hydrogen (C/H) atomic ratio, or heating value (net heat of combustion). The sensor comprises a constant-volume ignition chamber equipped for measuring ignition delay and magnitude of a peak rise in pressure or temperature following dispensation of a liquid fuel into the chamber. The sensor utilizes air at atmospheric pressure and microliter quantities of fuel. The sensor can be implemented in real-time refinery operations for blending diesel fuels that meet government mandated cetane number standards as well as in applications for standardizing jet, biodiesel, and synthetic fuels, which presently are not classified by any physicochemical property.

7 Claims, 7 Drawing Sheets

(56) References Cited

OTHER PUBLICATIONS

W. Helmore, "Spontaneous Ignition Temperatures: Determination and Significance," The Science of Petroleum, Oxford University Press, London, 1938, pp. 2970-2975.
R. W. Hurn and K. J. Hughes, "Combustion Characteristics of Diesel Fuels as Measured in a Constant-Volume Bomb," SAE Quarterly Transactions, 6 (1), 1952, pp. 24-35.
T. W. Ryan III, "Correlation of Physical and Chemical Ignition Delay to Cetane Number," SAE Technical Paper Series, No. 852103, (1985), pp. 1-13.
ASTM, Designation D6890-13b, "Standard Test Method for Determination of Ignition Delay and Derived Cetane Number (DCN) of Diesel Fuel Oils by Combustion in a Constant Volume Bomb", Oct. 1, 2013.
ASTM, Designation D7170-14, "Standard Test Method for Determination of Derived Cetane Number (DCN) of Diesel Fuel Oils—Fixed Range Injection Period, Constant Volume Combustion Chamber Method", May 1, 2014.
PAC Brochure, Herzog Cetane ID 510, Dec. 2015.

SENSOR FOR DETERMINING A PHYSICOCHEMICAL PROPERTY OF A LIQUID FUEL

CROSS REFERENCE TO RELATED APPLICATION

This application claims the benefit of U.S. Provisional Patent Application No. 62/346,606, filed Jun. 7, 2016.

GOVERNMENT RIGHTS

This invention was made with support from the U.S. government under Contract No. FA8650-13-M-2394, sponsored by the Department of Defense. The U.S. Government holds certain rights in this invention.

FIELD OF THE INVENTION

This invention pertains to an apparatus and method for determining a physicochemical property of a liquid fuel. In one application, this invention pertains to an apparatus and method for determining a cetane number of a liquid fuel. In another application, this invention pertains to an apparatus and method for determining carbon content and a carbon-to-hydrogen (C/H) atomic ratio of a liquid fuel.

BACKGROUND OF THE INVENTION

For a long time the field of fuel analysis has sought a rapid, accurate and reliable test method that employs a portable sensor for determining physical and chemical properties of a liquid fuel. Desirably, the method and sensor would be applicable to a wide variety of liquid fuels including those derived from conventional fossil fuels, such as diesel and jet propulsion fuels, and those derived from non-conventional resources, such as bio-based renewables and synthetic fuels from Gas-to-Liquid (GTL) and Fisher-Tropsch (FT) processes. As used herein, the term "physical property" is defined as a property of the fuel which upon determination under analytical test conditions does not change the identity of the fuel. In contrast, the term "chemical property" is defined herein as a property of the fuel which upon determination under analytical test conditions changes the identity of the fuel. As determined by the invention described herein, cetane number, carbon content, and carbon-to-hydrogen (C/H) atomic ratio are construed in this instance to be chemical properties. For purposes of this invention, the physical and chemical properties of a substance, taken individually or as a group, will be referenced hereinafter as "physicochemical properties".

Generally, diesel engines operate well with a fuel having a cetane number (CN) from 40 to 55. Fuels with higher cetane number have shorter ignition delays, providing more time for the subsequent fuel combustion process to be completed. Commercial diesel fuel is mandated by law to meet strict CN specifications, which vary with state and country in which the diesel fuel is sold. Modern day refineries in the United States must produce diesel fuel with a CN of at least 50. Batches of diesel having a cetane number less than the applicable mandated standard are blended with cetane enhancers to ensure meeting the mandated minimum and targets toward increasingly lower fuel emissions.

Under current refinery process protocols, fuel samples are sent for CN analysis and results are typically available in one or two days. This delay in obtaining the fuel's cetane number does not permit expeditious changing of process conditions and regulation of cetane enhancers for specific fuel batches and can lead to entire fuel batches being reworked due to a late discovery of product variances. As a result, cetane enhancers are added regardless of the need or lack thereof in a particular batch of fuel, due to the unavailability of a measurement device and method providing for cetane number analysis with rapid-turnaround. Often, the cetane number of a batch of diesel, measured after blending with the cetane enhancers, is considerably higher than the minimum required limit. These delays and problems could be avoided if the quality and physicochemical properties of batches of diesel fuel could be ascertained quickly and accurately in real-time. Cost savings would be significant inasmuch as cetane enhancers are very expensive, an order of magnitude more costly than current prices of crude oil per barrel.

Logistic fuels, such as liquid distillate fuels, including jet propulsion fuels JP-8 and JP-5, are used across a full range of internal combustion (IC) engines including conventional compression-ignited IC engines, Remote Piloted Aircraft (RPA) applications, and heavy duty compression ignition engines. Unlike commercial diesel, logistical jet fuels have no cetane specification and vary widely in this key measure of combustion property and quality assurance. Cetane number is correlated with a direct measure of ignition delay, which directly affects engine performance including fuel consumption, engine operability, and maintenance requirements. Variations in engine performance could be avoided if the logistic fuels could be evaluated with a portable fast-response cetane sensor.

Likewise, non-conventional liquid fuels have no cetane specification and vary widely in this key measure of combustion property and quality assurance. By "non-conventional liquid fuels", we include liquid fuels derived from renewable resources, for example bio-based fuels and synthetic liquid fuels derived from F-T and GTL processes. It should be appreciated that non-conventional fuels have different distributions of paraffinic and aromatic constituents as compared to petroleum-based fossil fuels, making it difficult to assess cetane numbers accurately. Yet, due to a growth in bio-based feedstocks and synthetic F-T and GTL processes, more non-conventional fuels are expected to be available to refineries in the future at relatively low cost; and therefore, having such fuels standardized by cetane number or other physicochemical property would be highly desirable.

Testing methods and apparatuses are known for measuring the ignition delay of diesel fuel and correlating the ignition delay with cetane number. A gold standard for such testing is defined by American Society of Testing Methods Test No. D-613 (ASTM D-613) using a single-cylinder four-stroke cycle, variable compression ratio Cooperative Fuel Research (CFR) diesel engine made by Waukesha. The apparatus is large, heavy, and non-portable, and requires high initial investment and high maintenance costs, special operator training, high fuel volume, and considerable testing time. Somewhat less complex testing methods are known, which measure ignition delay in a constant-volume bomb and correlate the ignition delay to a Derived Cetane Number (DCN), as disclosed for example in U.S. Pat. No. 4,549,815. This latter method is found commercially in a Herzog Cetane ID 510 apparatus available from PAC LP and an IQT™ Diesel Fuel Ignition Quality Tester available from Advanced Energy Technologies. These commercial apparatuses operate at high pressure with purified oxygen and require up to 1 liter of fuel for run times of at least twenty minutes, not including apparatus heat-up time. Moreover, the apparatuses measure ignition delay in milliseconds, thereby requiring a high resolution pressure detector.

The art would benefit from discovery of a compact and portable sensor that provides an analytical testing method for measuring the physicochemical properties of a liquid fuel, such as cetane number, carbon content, and C/H atomic ratio. More desirably, the sensor and testing method would provide rapid results in real-time with accuracy and precision (repeatability). It would be beneficial if the method were to consume less fuel than present day analytical methods and were to operate at ambient pressure on air, rather than pressurized oxygen. Such a method would be even more useful if it were capable of standardizing a wide variety of liquid fuels including gasoline, diesel, distillate, and jet propulsion fuels (JP-5, JP-8, Jet A) as well as bio-based renewable fuels and synthetic fuels including F-T and GTL fuels. For refinery applications, a real-time measurement capability would reduce delays and improve commercial fuel yields by performing in-situ real-time input material validation, quality monitoring, and product verification. Other end-user applications for such a sensor would include fuel quality verification, stored fuel integrity, laboratory fuel analysis, and quality checks on spot-purchased fuel. Moreover, a reliable testing method and sensor for determining physicochemical properties of a variety of liquid fuels would enhance modifications in engine parameters and improvements in engine performance across the range of commercial internal combustion engines.

SUMMARY OF THE INVENTION

We describe herein a novel sensor and testing method that provide a rapid, compact and uncomplicated manner for determination of a physicochemical property of a liquid fuel. Among the properties measured are included, but not limited to, carbon content, carbon-to-hydrogen atomic ratio (C/H atomic ratio), cetane number, and heating value (net heat of combustion) of the liquid fuel. One skilled in the art will appreciate that the term "cetane number" relates to a measure of quality of a diesel fuel, expressed as a percentage of cetane in a mixture of cetane and 1-methylnapthalene of the same quality as the given fuel, where 1-methyl-naphthalene is assigned a CN of 0 and cetane is assigned a CN of 100. Cetane number is an inverse function of a fuel's ignition delay, that is, the time period between the start of injection and the ignition and combustion of the fuel. Our invention beneficially expands upon the prior art by allowing the cetane number derived by this invention to be used to standardize not only light distillate fuels, such as diesels, but other liquid fuels including heavier distillates, such as jet propulsion fuels, and non-conventional fuels derived from bio-based renewables, such as biodiesels, and synthetic processes (F-T and GTL). Additionally, this invention beneficially provides for determination of whether a fuel of unknown origin was derived from a conventional fossil fuel or a non-conventional fuel resource.

In one aspect, therefore, this invention provides for a novel sensor for determining a physicochemical property of a liquid fuel, comprising:
(a) an ignition chamber having a ratio of surface-area-to-volume of greater than 4.7 per inch (1.9/cm);
(b) a fuel dispenser terminating within the chamber at a dispensing coordinate located at or about a geometric midpoint of the chamber in transverse and longitudinal directions;
(c) an inlet line disposed at one end of the chamber;
(d) an outlet line disposed at an opposite end of the chamber;
(e) a heater connected to an exterior wall of the chamber;
(f) at least one thermocouple connected to the chamber; and
(g) a pressure transducer disposed in the inlet line or outlet line.

In another aspect, this invention provides for a method of determining a physicochemical property of a liquid fuel, comprising the steps of:
(a) providing an ignition chamber having a ratio of surface-area-to-volume of greater than 4.7/inch (1.9/cm); and comprising an inlet line disposed at one end of the ignition chamber, and comprising an outlet line disposed at an opposite end of the ignition chamber;
(b) heating the ignition chamber to a preselected temperature;
(c) flushing an oxidant through the chamber from the inlet line to the outline line;
(d) closing said inlet and outlet lines and maintaining the oxidant and the chamber at the preselected temperature;
(e) dispensing a sample of a liquid fuel through a fuel dispenser into said chamber, the fuel dispenser terminating within the chamber at a dispensing coordinate located at or about a geometric midpoint of the chamber in transverse and longitudinal directions;
(f) recording a time of dispensing the liquid fuel;
(g) recording time and magnitude of a peak in pressure or temperature, that is, a pressure or temperature waveform, within the chamber after ignition of the liquid fuel;
(h) deriving from the recordings of steps (f) and (g) a physicochemical property of the liquid fuel.

In one embodiment, the sensor and method of this invention derive the cetane number of a liquid fuel based upon ignition delay, calculated as the difference between the time of dispensing the liquid fuel and the time at a point along the peak, i.e., waveform, as recorded in steps (g) and (f), respectively. In another embodiment, the sensor and method of this invention derive the carbon content of the liquid fuel based upon the magnitude of the peak derived in step (g). In yet another embodiment, the sensor and method of this invention derive the carbon-to-hydrogen (C/H) atomic ratio of the liquid fuel based upon the magnitude of the peak derived in step (g). In yet another embodiment, the sensor and method of this invention derive the heating value (net heat of combustion) of the liquid fuel based upon the magnitude of the peak derived in step (g).

As described herein, the sensor and sensing method of this invention beneficially provide accurate and reliable information on physicochemical properties of a liquid fuel including, but not limited to cetane number, carbon content, carbon-to-hydrogen (C/H) atomic ratio, heating value (net heat of combustion), and octane number. It should be appreciated that the apparatus is beneficially constructed in a compact and miniaturized size for use in quality control applications of any type and location including on-site refinery fuel blending applications, remote logistics fuel testing applications, fuel storage applications, and on-site fuel sales applications. Moreover, the method of this invention operates quickly in real-time thereby eliminating delays in waiting for fuel quality control analyses. Advantageously, the method of the invention operates with air at ambient pressure, as opposed to pressurized oxidant, such as oxygen and air, and consumes considerably less fuel as compared with present day cetane number testing methods and apparatuses.

The sensor apparatus and method of this invention find application in standardizing liquid fuels of a wide composition range from diverse resources, including conventional fossil-fuel based diesel, distillate and jet propulsion fuels as well as less conventional biodiesels and GTL and F-T liquid fuels. For fuel production applications, such as in refineries, a real-time on-line measurement capability aids in improving yield by performing input material validation, quality monitoring, and product verification. Other end-user applications include fuel quality verification, stored fuel integrity, laboratory fuel analysis, and quality check on spot-purchased fuel.

DETAILED DESCRIPTION OF THE INVENTION

The skilled person in the art will appreciate that the general description of the invention, as provided hereinabove, can be realized in various and different embodiments. In one such embodiment of the invention, there is provided a novel sensor for determining a physicochemical property of a liquid fuel, comprising:

(a) an ignition chamber having an aspect ratio of longest dimension to shorter dimension(s) greater than about 2.1:1 and having a ratio of surface-area-to-volume of greater than 4.7 per inch (1.9/cm);
(b) a fuel dispenser terminating within the chamber at a dispensing coordinate located at or about a geometric midpoint of the chamber in transverse and longitudinal directions;
(c) an inlet line disposed at one end of the chamber;
(d) an outlet line disposed at an opposite end of the chamber;
(e) a heater connected to an exterior wall of the chamber;
(f) at least one thermocouple connected to the chamber;
(g) a pressure transducer disposed in the inlet line or outlet line; and
(h) a data analysis control unit configured to (i) control a time of dispensing said liquid fuel into the chamber; (ii) record time and magnitude of a peak in pressure or temperature within the chamber after dispensing the liquid fuel; (iii) derive from said recordings of step (ii) a physicochemical property of the liquid fuel.

In a related embodiment, there is provided a method of determining a physicochemical property of a liquid fuel, comprising the steps of:

(a) providing an ignition chamber having an aspect ratio of longest dimension to shorter dimension(s) of greater than about 2.1:1 and having a ratio of surface-area-to-volume of greater than 4.7/inch (1.9/cm); and comprising an inlet line disposed at one end of the ignition chamber, and comprising an outlet line disposed at an opposite end of the ignition chamber;
(b) heating the ignition chamber to a preselected temperature;
(c) flushing an oxidant through the chamber from the inlet line to the outline line;
(d) closing said inlet and outlet lines and maintaining the oxidant and the chamber at the preselected temperature;
(e) dispensing a sample of a liquid fuel through a fuel dispenser into said chamber, the fuel dispenser terminating within the chamber at a dispensing coordinate located at or about a geometric midpoint of the chamber in transverse and longitudinal directions;
(f) recording a time of dispensing the liquid fuel;
(g) recording time and magnitude of a peak in pressure or temperature within the chamber after dispensing the liquid fuel into the chamber; and
(h) calculating an ignition delay as the difference between the time of fuel dispensing and the time at a point along the peak; and
(i) deriving from said ignition delay or said magnitude of said peak in pressure or temperature a physicochemical property of the liquid fuel.

Figure 1:
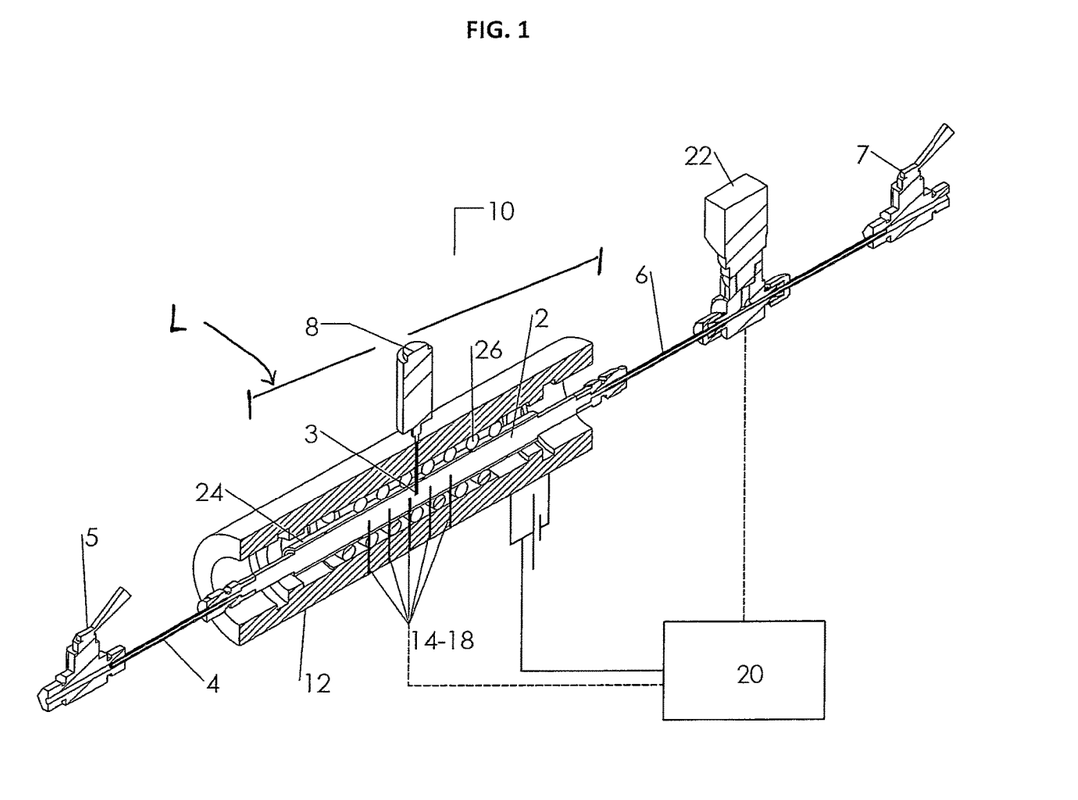
FIG. 1 illustrates an isometric view of an embodiment of the apparatus of this invention.

With reference to FIG. 1, an embodiment 10 of the sensor apparatus of this invention is depicted in isometric section, comprising a cylindrical ignition chamber 2 of length "L" (z-axis) having disposed on one end an inlet line 4 including an open/shut valve 5 for feeding into the chamber a flow of oxidant or sweep gas or a flow of a mixture of oxidant and sweep gas. The apparatus further comprises an outlet line 6 including an open/shut valve 7 for exiting flow gas from the chamber 2, including oxidant, sweep gas, a mixture of oxidant and sweep gas, and combustion products. In this embodiment, inlet line 4 and outlet line 6 are disposed at opposite ends of the length L or longest dimension of the ignition chamber 2 to allow for thorough flow of gases throughout the chamber. The sensor apparatus 10 further comprises a fuel dispenser 8 secured at or about a midpoint (+/−15 percent) along the length "L" of the ignition chamber 2. The fuel dispenser terminates within ignition chamber 2 at fuel dispensing tip 3 terminating within the chamber 2 at a position distant from any interior wall of the chamber, which means that the point of injection is positioned to reduce contact of the liquid fuel with the walls of the chamber. The sensor 10 further comprises an electronically-controlled heating tape 26 circumscribed around an exterior wall 24 of the cylindrical ignition chamber 2. A plurality of thermocouples 14-18 are secured to the ignition chamber 2 and also connected to data analysis control unit 20. In the embodiment shown in FIG. 1, the thermocouples penetrate the chamber wall and terminate within ignition chamber 2. Ignition chamber 2 and heating tape 26 are enclosed in exterior housing 12, which may consist of an insulating material. Pressure transducer 22 is installed in outlet line 6 and further connected to data analysis control unit 20.

Figure 2:
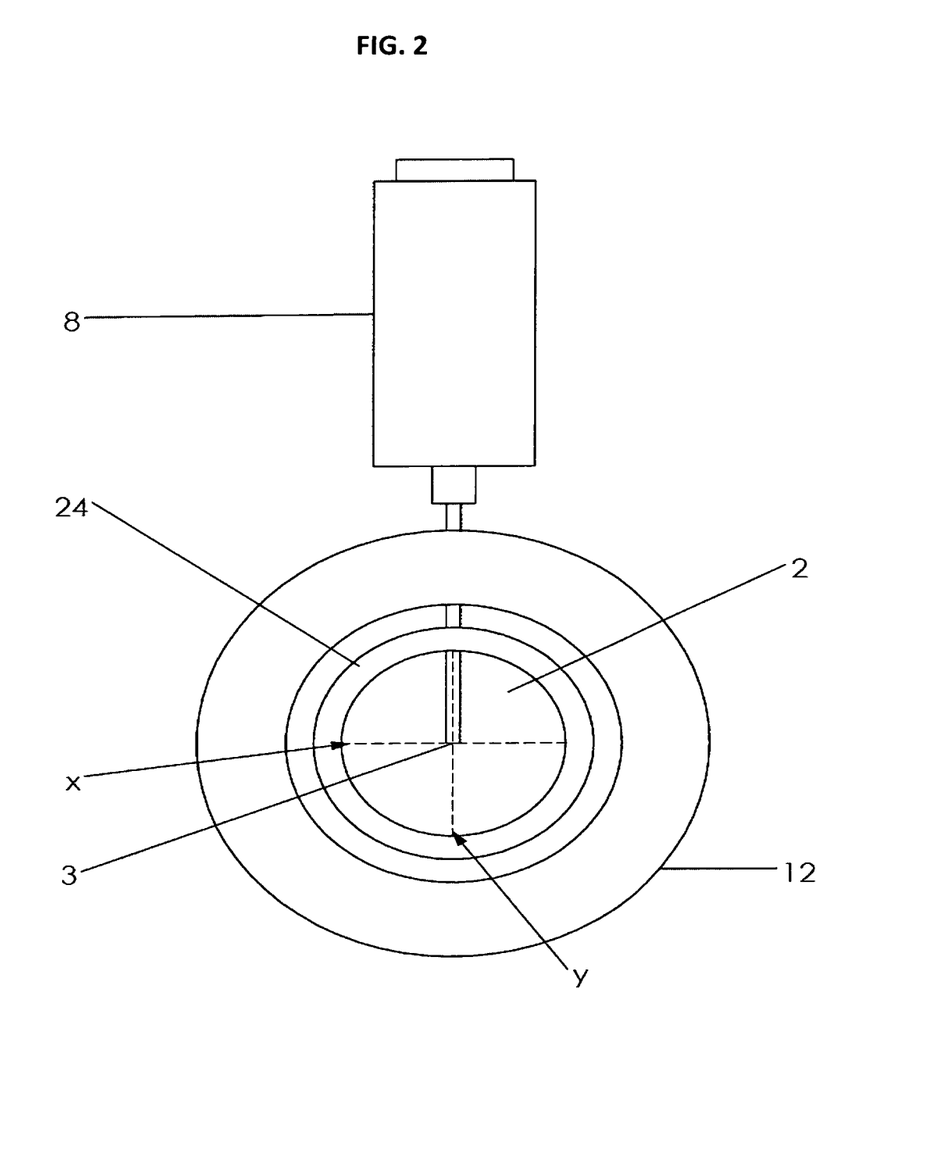
FIG. 2 illustrates a transverse view of an embodiment of the dispenser and dispensing coordinate of the apparatus of FIG. 1.

In FIG. 2 an enlargement of fuel dispensing tip 3 of fuel dispenser 8 is illustrated in transverse section as viewed along inlet line 4 of the sensor apparatus 10. As illustrated in FIG. 2, the fuel dispensing tip 3 is positioned within ignition chamber 2 as defined by cylinder 24 set within housing 12, for the purpose of reducing contact of the liquid fuel with the walls of the chamber. The tip position 3 is specified herein by a "dispensing coordinate" defined by coordinates (x, y) as seen in FIG. 2, that is, positions along a horizontal (x) axis and a vertical (y) axis of the transverse section of the ignition chamber 2. To accomplish these objectives, the fuel dispensing tip 3 terminates within the ignition chamber 2 at a dispensing coordinate about midway along both horizontal and vertical transverse axes of the ignition chamber 2. The words "about midway" mean that the tip 3 is located at a distance 50 percent along the vertical (y-) axis and 50 percent along the horizontal (x-) axis of the ignition chamber plus or minus 15 percent along either coordinate, i.e., (50%±15%). Moreover, to reduce atomization of the fuel, the fuel dispenser 8 preferably operates in absence of elevated back pressure such as would be present in high pressure fuel injector devices.

Figure 3:
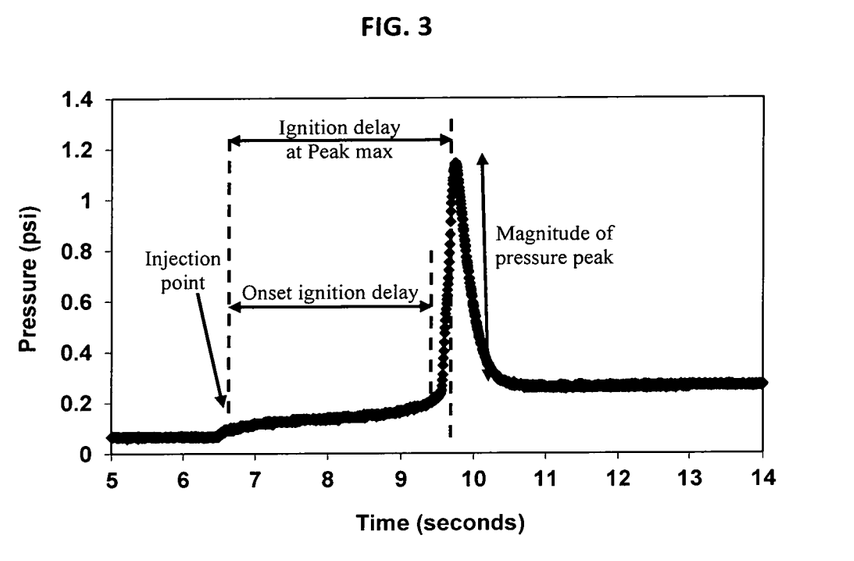
FIG. 3 depicts a graph plotting pressure versus time in an embodiment of the method of this invention.
Figure 4:
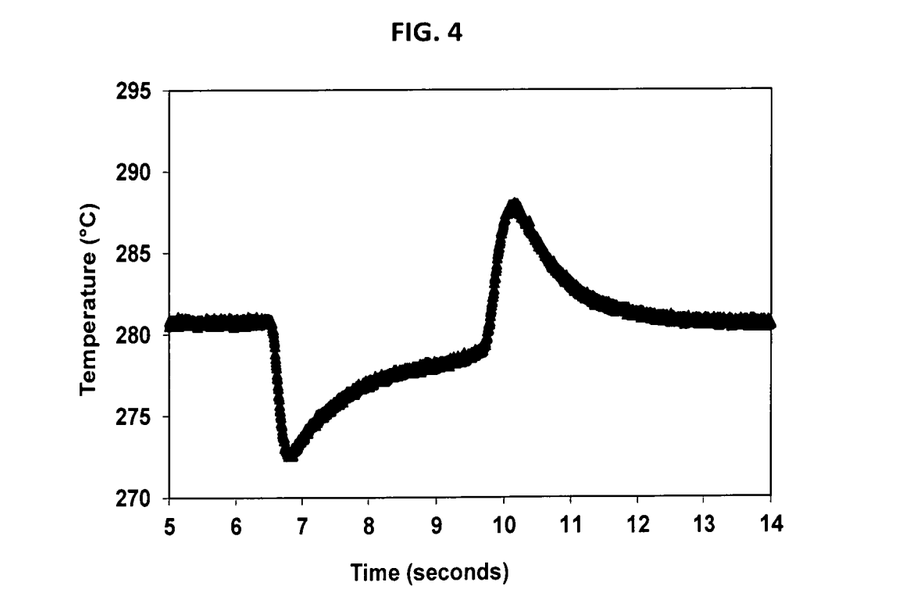
FIG. 4 depicts a graph plotting temperature versus time in an embodiment of the method of this invention.

With further reference to FIG. 1, sensor 10 operates by implementing the following steps: Valves 5 and 7 on inlet and outlet lines 4 and 6, respectively, are turned to open positions so as to provide a flow path from the inlet line 4 through ignition chamber 2 to outlet line 6. The heating tape 26 is energized and the ignition chamber 2 is heated to a preselected temperature as measured by thermocouples 14-18. Once the desired temperature is stabilized throughout the ignition chamber, an oxidant, which may or may not include a sweep gas, is passed at ambient pressure from the inlet line 4 through the chamber to outlet line 6, until the chamber is thoroughly flushed and cleared of any extraneous gases. Thereafter, valves 5 and 7 are closed; and after the desired temperature is re-stabilized throughout the chamber, the fuel dispenser 8 is engaged to dispense a sample of liquid fuel into the chamber 2. As seen in FIG. 3, a small rise is pressure is detected at the pressure transducer 22 upon dispensing or injection of the fuel, and the time at which the small increase in pressure occurs is recorded at data analysis control unit 20 as the time of fuel dispensation or injection. Simultaneously, as seen in FIG. 4, a decrease in temperature is detected upon dispensing the fuel, due to the fuel being heated and vaporized. After a period of some seconds, a large increase in pressure develops and is detected at the pressure transducer 22, as seen in FIG. 3; as well a large increase in temperature develops and is detected as seen in FIG. 4. These data are likewise recorded at the data analysis control unit 20. The onset of the pressure and temperature increase is taken as the post-injection time at which a measurable rise or deviation above baseline is recorded; such onset being correlated with fuel ignition. As the fuel combusts, the pressure and temperature reach a maximum and afterwards decline. These pressure and temperature waveforms, referred to as "peaks", are likewise recorded at the data analysis control unit 20, which then calculates the difference between the time of fuel dispensing and the time at any selected point along the peak. The difference is recorded as the ignition delay, which is then correlated with a physicochemical property of the liquid fuel, namely, cetane number. In a first embodiment, the ignition delay is calculated as the difference between the time of dispensing the liquid fuel and the time at onset of the peak, as shown in FIG. 3. The onset of the peak can be determined in various ways. In one embodiment, the onset is taken as the time wherein a tangent line drawn at about a 45 degree angle to the baseline contacts the rising side of the peak. In other embodiments, the angle of the tangent line is varied from the 45 degree angle depending upon the shape of the peak and the length of the ignition delay. In other approaches, the onset of the pressure or temperature peak is determined by evaluating a first derivative of the pressure or temperature with respect to time, respectively, dP/dt or dT/dt. In another embodiment of the invention, the ignition delay is calculated as the difference between the time of dispensing the liquid fuel and the time at maximum magnitude of the peak, as also shown in FIG. 3. In a third embodiment, the data analysis control unit 20 calculates the maximum magnitude of the peak increase in pressure or temperature and correlates the maximum magnitude with one or more physicochemical properties of the liquid fuel, such as C/H ratio or carbon content or heating value. Other embodiments defining the time at onset of the peak or the time at any other selected point along the peak are possible, including those derived from known mathematical manipulations of such data, such as, evaluating first or second derivatives of the peak. Within each set of experiments, it is recommended to employ the same methodology consistently when selecting the time at a point along the peak. After ignition, combustion, and analysis of the aforementioned data, valves 5 and 7 of inlet line 4 and outlet line 6 are opened; and the ignition chamber 2 is flushed with sweep gas until combustion products, unreacted oxidant and trace unreacted fuel, if any, are flushed out of the chamber. Typically, the process steps of this invention are repeated one or more times to ensure accuracy and precision of measurement. If on subsequent test runs, a different preselected temperature is desired, the apparatus is heated or cooled to the new temperature before the procedure is repeated.

The data analysis control unit 20 comprises a digital computer, which is configured to regulate the pre-injection temperature of the chamber; record measured temperatures and pressure with the chamber; determine a time of fuel injection or dispensation; record the times at onset and development of the peak in pressure, temperature, or both within the chamber; record the magnitude of the peak rise in pressure, temperature, or both temperature and pressure; calculate the ignition delay as described hereinabove; and correlate said data with properties of the liquid fuel based on calibration curves stored in the computer. The calibration curves are obtained from observation of ignition delay and peak magnitude for liquid fuels of known physicochemical properties, that is, known cetane number, C/H ratio, carbon content and the like as obtained using qualified ASTM methods.

The ignition chamber is constructed of any explosion-proof material capable of withstanding the temperature and pressure to which the chamber is exposed under ignition and combustion conditions. Suitable materials include stainless steel, Inconel alloy, Hastelloy® brand alloy, and a combination thereof. The chamber can be constructed in any shape providing that the shape meets requirements for surface-area-to-volume ratio as detailed hereinafter. One suitable shape is a cylindrical rod; another suitable shape is a rod provided in an elliptical shape or rectangular shape. Likewise, the dimensions of the ignition chamber can be scaled up or down as desired, provided that requirements are met for surface-area-to-volume ratio. The smaller the chamber, the more portable the apparatus will be. As a consequence, the ignition chamber in one embodiment comprises a rod having a length in a range from about 2 cm to about 16 cm and a diameter ranging from about 1.3 cm to about 2.5 cm. In such miniaturized form, the weight of the ignition chamber typically does not exceed 1.1 pounds (500 grams).

More important than the actual dimensions is the surface-area-to-volume ratio of the ignition chamber. For this invention, the surface-area-to-volume ratio is typically greater than 4.7 per inch (1.9/cm) and, preferably, ranges from greater than about 4.7 per inch (1.9/cm) to less than about 6.0 per inch (2.4/cm). The surface area of a rod-shaped ignition chamber is calculated as the sum of the surface areas of the interior of the rod and the two end caps on the rod. In another feature, the apparatus of this invention employs an aspect ratio of length L of longest dimension (z-axis) relative to individual lengths of two other dimensions (x- and y-axes) of greater than about 2.1:1, preferably, greater than about 2.5:1. The aspect ratio is typically less than about 8.3:1, preferably, less than 6.0:1.

The inlet and outlet lines are constructed of standard stainless steel piping and are fitted to the open/shut flow valves and the ignition chamber with conventional Swagelock® brand fittings and interconnects. Conventional open/shut flow valves are fitted into each flow line to control the flow into and out of the ignition chamber. Standard K-type thermocouples (e.g., Omega Engineering, Inc.) are attached along the outer wall of the ignition chamber with penetration through the chamber wall and termination within the chamber; and the chamber is covered with a commercially available heating tape or cable (e.g., McMaster-Carr Supply Company) for heating the ignition chamber to a preselected temperature in a range between about 230° C. and about 350° C. A stock pressure transducer is employed operating in a range from 0 to 15 psia, as commercially available, for example, from Honeywell Industries.

In describing the fuel delivery device, the prior art often refers to a fuel "injector" and fuel being "injected" into a combustion chamber. The time at which the fuel is injected is referenced as the "injection time". In a broad sense our invention also employs a "fuel injector" that "injects" fuel into the sensor chamber; and we can refer to our fuel delivery device as an "injector". For preferred embodiments, we prefer to use the terms "fuel dispenser" and "dispensing" to emphasize differences between the fuel delivery system of this invention and the fuel delivery system of the prior art. On the other hand, we refer to the time at which the fuel is dispensed into the chamber as the "time of dispensing" or, in the alternative, the "injection time" simply to adhere to convention in this subject technology.

More specifically, the prior art discloses a high pressure fuel injector, such as those operating at 100 to 1,500 barg (150 MPag). This type of fuel injector delivers and atomizes a sample of fuel with high back-pressure delivered with aid of an injection gas. With such a device, the fuel is prone to splash and contact the interior walls of the chamber, thereby producing undesirable coking resulting in lower accuracy and reduced repeatability under test conditions. In contrast, the fuel dispensing system of this invention consists of a comparatively lower pressure fuel dispensing device such as a micro-syringe, for example, a micro-syringe of the type sold by Hamilton (Model 1710, 100 µl) or a micro-repeating dispenser, for example, of the type also sold by Hamilton Company (Model no. PB600-1), delivering an accurate quantity of fuel ranging in volume from about 0.5 microliter (0.5 µl) to about 50 Such dispensing systems deliver the fuel into the ignition chamber at low back-pressure as a liquid droplet without the aid of an injection gas, which in turn minimizes atomization and splashing of the fuel onto the interior walls of the chamber. By employing the gentle fuel dispenser of this invention in combination with microliter volumes of liquid fuel and sufficiently high operating temperatures, the fuel simply volatilizes and dissipates through the chamber reducing coking and improving accuracy and repeatability under test conditions. The design of the invention allows for miniaturization of overall equipment size that has broad applicability heretofore unseen in the prior art.

Any liquid fuel suitable for use in an internal combustion engine is suitably employed in the method of this invention including those derived from conventional fossil fuels, such as gasoline, kerosene, diesels including ULSD and Tier 2 diesels, and other liquid distillate fuels including jet propulsion fuels, such as Jet A, JP-5, and JP-8, and military fuels, as well as pure component fuels such as, but not limited to, n-dodecane, hexadecane, and heptamethylnonane. Other suitable fuels include those derived from non-traditional resources such as renewable and synthetic sources including biodiesels, high renewable jet fuels (HRJ), fuels prepared by synthetic methods from synthesis gas, such as Fisher-Tropsch (F-T) fuels and gas-to-liquid (GTL) fuels. In one preferred embodiment, the fuel is a liquid distillate fuel selected from diesel and jet propulsion fuels as noted above. It should be appreciated that the petroleum-based fossil fuels typically contain a very large number of aromatic, paraffinic, and cycloparaffinic compounds, the aromatic content of which may exceed 20-30 weight percent. By comparison, biodiesel fuels derived from biological materials and F-T fuels prepared from synthesis gas contain fewer chemical components and include a higher paraffinic content and a lower aromatic content.

The fuel employed in the method of this invention can have any cetane number, carbon content, carbon-to-hydrogen (C/H) atomic ratio, and heating value as may be known and found for such fuels. Generally, the cetane number of the fuel employed in this invention ranges from about 15 to 100. Generally, the carbon content of the fuel employed in this invention ranges from about 84 to about 87 percent by weight, based on the total weight of the liquid fuel. Generally, the carbon-to-hydrogen (C/H) atomic ratio of the fuel employed in this invention ranges from about 0.45:1 to about 0.55:1. It should be appreciated that the sensor of this invention is designed to measure such properties as cetane number, carbon content, and C/H atomic ratio, as well as other physicochemical properties including but not limited to heat content (net heat of combustion) and octane number.

The quantity of liquid fuel sample employed in the method of this invention is typically greater than about 0.5 microliter (0.5 µl), preferably greater than about 1.0 µl, more preferably greater than about 1.8 µl. The quantity of liquid fuel sample employed in the invention is typically less than 50 µl, preferably less than about 25 µl, and more preferably less than about 10 µl.

The oxidant employed to ignite the distillate fuel is selected from molecular oxygen, or any mixture of oxygen and nitrogen, preferably air, or any mixture of oxygen and an inert gas, such as helium, argon, or carbon dioxide. Generally, oxygen or air is employed. More desirably, the method of this invention employs air at ambient, i.e. atmospheric, pressure as the oxidant. Since the quantity of oxygen in the chamber far exceeds the quantity of fuel added to the chamber, the ratio of oxygen relative to carbon in the fuel is typically greater than the stoichiometric ratio needed for full combustion of the fuel, a condition that is described as "fuel-lean". Given that essentially no coke is seen to accumulate within the sensor chamber over multiple tests, it is believed that virtually all of the fuel is combusted.

The sweep gas employed to flush the ignition chamber comprises any inert gas alone or in admixture with oxygen, suitable sweep gases including, but not limited to, nitrogen, helium, and argon, as well as any mixture of the aforementioned gases with oxygen. Nitrogen provides a preferred sweep gas, alone or in combination with oxygen. Beneficially, the oxidant and sweep gas are one and the same and provided as air.

The apparatus is flushed with oxidant or with a mixture of sweep gas and oxidant at a preselected chamber/sensor temperature and at atmospheric pressure. Preselected temperatures fall typically in a range from about 230° C. to about 330° C. Ambient pressure is taken as 1 atm absolute +/−0.1 atm (101 kPa+/−10 kPa). Flushing is continued for a time sufficient to thoroughly remove residual gases within the chamber, filling the chamber essentially with oxidant or mixture of sweep gas and oxidant, as desired.

After the sensor apparatus is flushed with oxidant at the preselected temperature, the inlet and outlet lines are closed and the chamber is given an acceptable time, typically up to about fifteen minutes, to equilibrate. Then, the sample of liquid fuel is dispensed into the chamber. It should be appreciated that the fuel is dispensed at the midpoint (+/−15 percent) of the three dimensions of the ignition chamber, thereby providing for essentially symmetrical heating and vaporization of the fuel within the chamber. The dispensation method reduces contact and deposition of the fuel on the interior walls of the chamber, thereby minimizing or eliminating unsymmetrical heating, hot spots, and coke formation.

As seen in FIG. 3 and FIG. 4, a small peak is recorded as a rise in pressure or a decrease in temperature following dispensing or injection of the fuel into the chamber. The small peak is recorded in the data control unit as the time of dispensation or injection of the fuel. Thereafter, the pressure and temperature of the chamber are recorded as a further function of time; and at a time post-fuel injection a large peak is recorded due to a large rise in pressure and temperature as the fuel combusts. The data analysis control unit calculates the difference in time between the time of injection and the time at a point along the peak, for example, peak onset at ignition or other point along the peak during combustion, the difference being recorded as the ignition delay. Additionally, the data analysis control unit calculates the magnitude of the peak rise and stores such said data for each test run. In this invention, typical ignition delays range between about 0.7 second to about 15 seconds. It should be appreciated that in a preferred embodiment of this invention the pressure sensing transducer operates at or about atmospheric pressure as opposed to high pressure and measures ignition delay in seconds rather than microseconds.

Referring to the embodiment illustrated in FIG. 1, the apparatus is conveniently controlled by the data analysis control unit 20 comprising a digital computer, which records the data as shown in FIG. 3 and FIG. 4 as described hereinbefore. A microprocessor in the data analysis control unit controls the fuel dispensing system (micro-syringe 8), which supplies fuel samples at precise amount to the ignition chamber. Pressure transducer 22 and the plurality of thermocouples (14-18) are connected to the microprocessor which records and calculates the ignition delay and the magnitude of the peak pressure and temperature. The microprocessor calculates the ignition delay as a function of chamber temperature prior to fuel injection. A plotter/printer is provided to produce outputs. An input device, such as a keyboard, supplies the starting parameters to the microprocessor, input parameters to include the desired temperature for each test measurement, the size of the fuel sample, the number of tests per temperature setting, and the temperature interval in between data points. Input data should also include the kind of fuel, namely, conventional fuel (e.g., diesel or distillate) or non-conventional fuel (e.g., biodiesel or F-T), inasmuch as calibration curves stored in the microprocessor will vary not only with temperature but also with fuel type. After the ignition delay or magnitude of the measured peak is determined, the microprocessor compares the measured data with the calibration curves to determine the property of the fuel. Cetane number is correlated with ignition delay; whereas carbon content, C/H atomic ratio, and heating value of the fuel are correlated with peak magnitude.

The sensor and method of this invention provide accurate information on the physicochemical properties of the liquid fuels tested. As one example, cetane number in a range from about 15 to about 65 is determined in this invention with a reproducibility of about +/−0.5 or better and with an accuracy of about +/−2, which compares very well with the accuracy (+/−2) in cetane number determined by standard qualified methods, such as ASTM D-613 and ASTM D-6890. Other physicochemical properties, such carbon content, C/H atomic ratio, and heating value of the fuel, can be determined with a similar degree of reproducibility and accuracy.

EMBODIMENTS

Example 1

With reference to FIG. 1, an embodiment of the sensor apparatus of this invention 10 was constructed from a cylindrical tube (stainless steel; length 15.24 cm; internal dia. 1.91 cm; internal volume 43.6 ml), which provides for a fixed-volume ignition chamber 2 defined by cylindrical structure 24. With these dimensions, the ignition chamber 2 had an aspect ratio of 8:1 and a surface-area-to-volume ratio of 5.7/inch (2.2/cm). The surface area of the cylindrical tube is calculated as the sum of areas of the interior wall of the cylindrical tube 24 and its two end caps. Five thermocouples 14-18 (K type) were connected along the length of the tube for measuring temperature, the measurements of which were transmitted to data control unit 20. A fuel injection port 8 (micro-syringe type and repeating dispenser sold by Hamilton) was fitted at the midpoint of the length of the cylindrical tube 24. The tip of the fuel dispenser terminated within the ignition chamber 2 at a point 3 midway along the length L (z-axis) of the cylinder 24 and at the midway point of the vertical and horizontal transverse axes (x, y) of the cylinder 24, as seen in FIG. 2. One end of the ignition chamber 2 was fitted using standard Swagelock® brand connections and interconnects with an inlet flow line 4 comprised of standard piping (stainless steel) equipped with an open/shut valve 5 for feeding into chamber 2 a flow of oxidant or sweep gas or a flow of a mixture of oxidant and sweep gas. The opposite end of chamber 2 was fitted likewise with an outlet flow line 6 including open/shut valve 7 for exiting gases from the chamber 2. An electronically-controlled heating tape 26 was wrapped around the exterior of the chamber 2 and also connected to data analysis control unit 20 for regulating temperature within the chamber. The ignition chamber 2 and heating tape 26 were housed in insulated housing structure 12. Thermocouples 14-18 were equally spaced along the length of the ignition chamber 2, with the thermocouple probes terminating within the ignition chamber spaced-apart from any interior wall of the chamber. A pressure transducer 22 (Honeywell) operating in a pressure range from 0 to 15 psia (0-103 kPa) with a resolution of +/−0.05 percent accuracy was installed in outlet line 6 and further connected to data control unit 20.

Operation of sensor 10 was conducted as follows: The ignition chamber 2 was swept with air at atmospheric pressure, with both inlet and outlet valves 5 and 7, respectively, in open position until the chamber was cleared of extraneous gases. With the air flow in progress and valves 5 and 7 in open position, the ignition chamber 2 was brought to a preselected temperature with an axial uniformity of +/−3° C. using heating tape 26 and thermocouples 14-18. Thereafter, the chamber was isolated by closing inlet valve 5 and outlet value 7, and a slug of fuel (2 µl) was dispensed into the center of the ignition chamber 2. The time of injection corresponded to t=0 on the time graph. Refer to FIGS. 3 and 4. The quantity of air versus the quantity of fuel injected corresponded to a large excess of oxygen relative to fuel (fuel-lean). A temperature decline was observed associated with heating and vaporizing the dispensed fuel. A modest pressure increase was observed associated with dispensing and heating the fuel in the fixed volume of the chamber 2. The time of the peak in temperature decline and pressure increase is taken as a time of dispensing the fuel (likewise, "time of injection"). At a time thereafter, a sharp spike occurred in temperature and pressure measurements corresponding to the ignition and combustion event. The time between the fuel injection and the maximum magnitude of the peak was taken as the "ignition delay" as seen in FIGS. 3 and 4. Data graphed in FIGS. 3 and 4 were stored in data control unit 20. The inlet and outlet valves 5 and 7 were thereafter opened and the chamber 2 was flushed with air until all residual combustion gases from the test were swept out. Then, the temperature of the chamber 2 was adjusted, as desired, and the valves were closed and the test repeated with another sample of the fuel or a different fuel.

Figure 5:
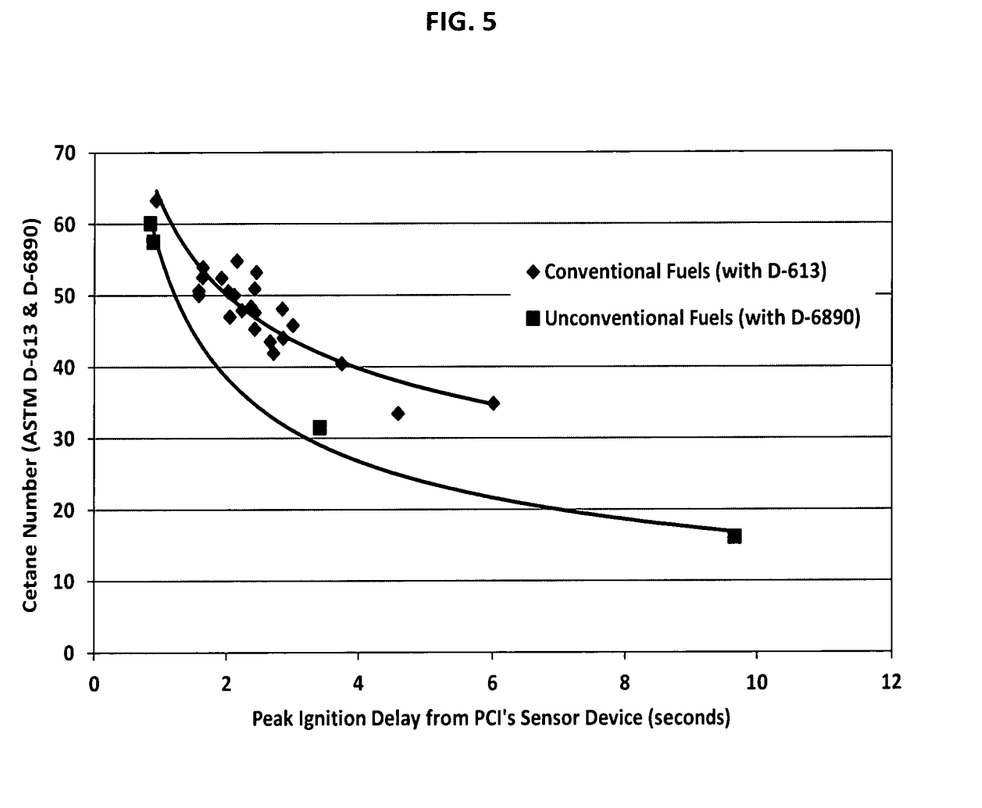
FIG. 5 depicts, for a set of liquid fuels, a calibration curve plotting known cetane number derived from ASTM methods versus ignition delay as measured in an embodiment of this invention.

The above procedure was employed to test a set of conventional diesel and distillate fuels of known cetane number ranging from 25 to 64 as determined by ASTM D-613, obtained from commercial and government suppliers. Ignition delay for each fuel was measured at 300° C. FIG. 5 depicts a calibration curve plotting the cetane number of the aforesaid conventional fuels as determined by ASTM D-613 versus peak ignition delay as determined by this invention. It is seen from FIG. 5 that as the known cetane number of the conventional fuel decreases, the peak ignition delay measured by this invention increases.

Example 2

Figure 6:
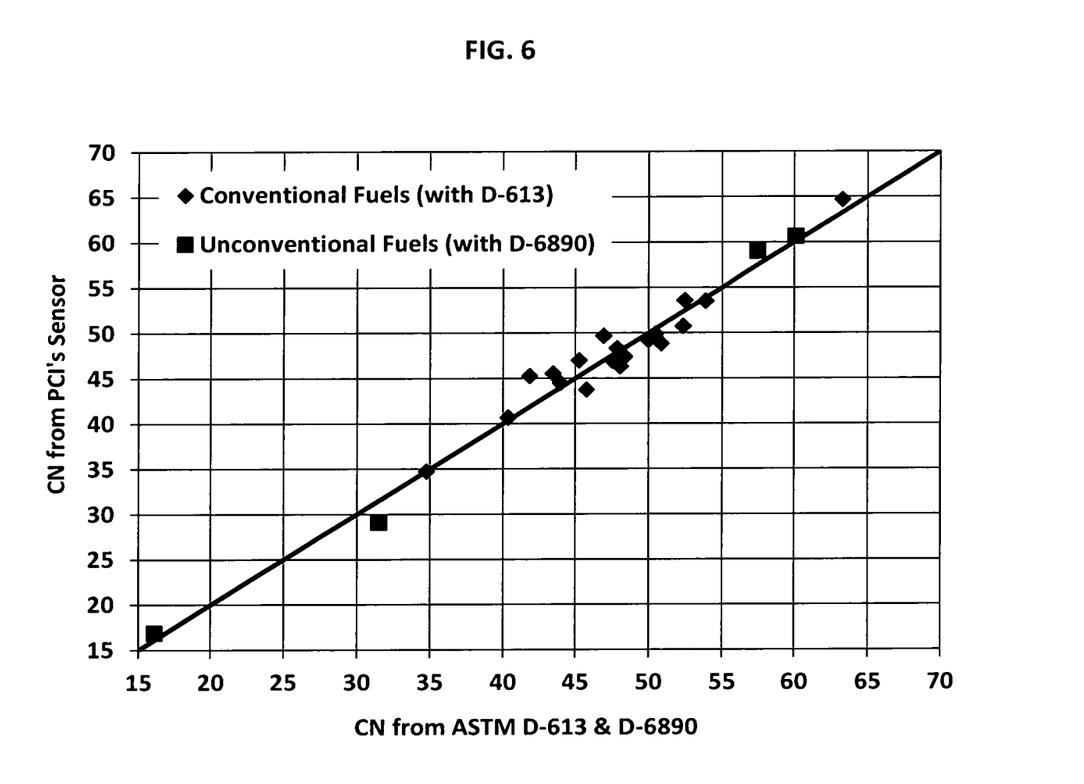
FIG. 6 depicts, for a set of liquid fuels, a graph plotting cetane number determined by the method of this invention versus cetane number as determined by cetane testing method ASTM D-613 or ASTM D-6890.

The method of this invention as described in Example 1 was employed to measure the cetane number of a set of diesel and distillate fuels. The tests were run blind, meaning that the inventors did not have advance knowledge of the cetane number of each fuel. Instead, the inventors presented cetane number as determined by the apparatus and method of this invention to the supplier of each fuel, who thereafter in return supplied the cetane number for the fuel as determined by ASTM D-613. FIG. 6 is a graph plotting cetane number of each conventional fuel as determined by this invention versus the cetane number as measured by ASTM D-613. It is seen that the graph points lie on a straight 45 degree line representing essentially 1:1 correlation between the sensor of the current invention and the accepted ASTM method. This result indicates that the cetane numbers obtained from the sensor and method of this invention lie very close to the cetane numbers determined by ASTM D-613.

Example 3

Example 1 was repeated with the exception that a set of unconventional fuels including biodiesel fuels and Fischer-Tropsch fuels were employed in place of the conventional fuels of E-1. Ignition delay was measured in the apparatus of this invention for each fuel at 300° C. FIG. 5 depicts a calibration curve plotting the cetane number for each unconventional fuel as determined by ASTM D-6890 versus peak ignition delay as determined by this invention. It is seen from FIG. 5 that as the known cetane number of the unconventional fuel decreases, the peak ignition delay as measured by this invention increases.

Example 4

The method of this invention as described in Example 1 was employed to measure the cetane number of a set of unconventional fuels including biodiesels and Fisher-Tropsch fuels. The tests were run blind, meaning that the inventors did not have advance knowledge of the cetane number. Instead, the inventors presented cetane number for each fuel as determined by this invention to the supplier of the fuel, who thereafter in return supplied the cetane number for the fuel as determined by ASTM D-6890. FIG. 6 depicts a graph plotting the cetane number of each unconventional fuel as determined by this invention versus the cetane number as measured by ASTM D-6890. It is seen that the graph lies on an essentially straight 45 degree line indicating that the cetane numbers obtained from the sensor and method of this invention lie very close to the cetane numbers determined by standard method ASTM D-6890.

Example 5

The sensor and method of this invention were employed as described in Example 1, with the exception that 7 fuel samples were employed, 3 being unconventional biodiesel or F-T fuels and 4 being conventional fossil fuel-based diesel or distillate fuels. Table 1 presents the carbon content and C/H ratio of each fuel tested.

TABLE 1

| Fuel Type | Carbon Content (wt. %) | C/H Ratio |
|---|---|---|
| Biodiesel | 84.7 | 0.461 |
| Biodiesel/biojet | 84.7 | 0.461 |
| F-T | 84.6 | 0.458 |
| ULSD (ultra-low sulfur diesel) | 86.54 | 0.546 |
| Tier 2 Diesel | 85.8 | 0.504 |
| JP-8 | 85.6 | 0.495 |
| JP-5 | 86.6 | 0.539 |

Figure 7:
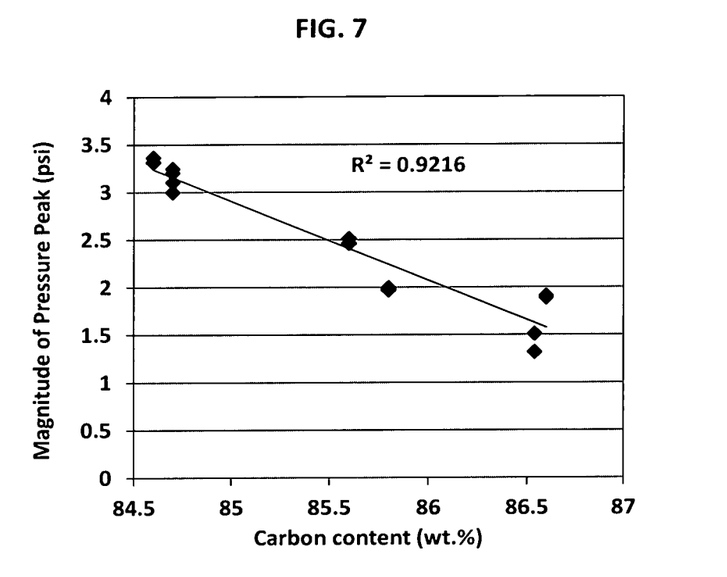
FIG. 7 depicts, for a set of liquid fuels, a calibration curve plotting magnitude of pressure peak as measured by this invention versus known carbon content for each fuel.
Figure 8:
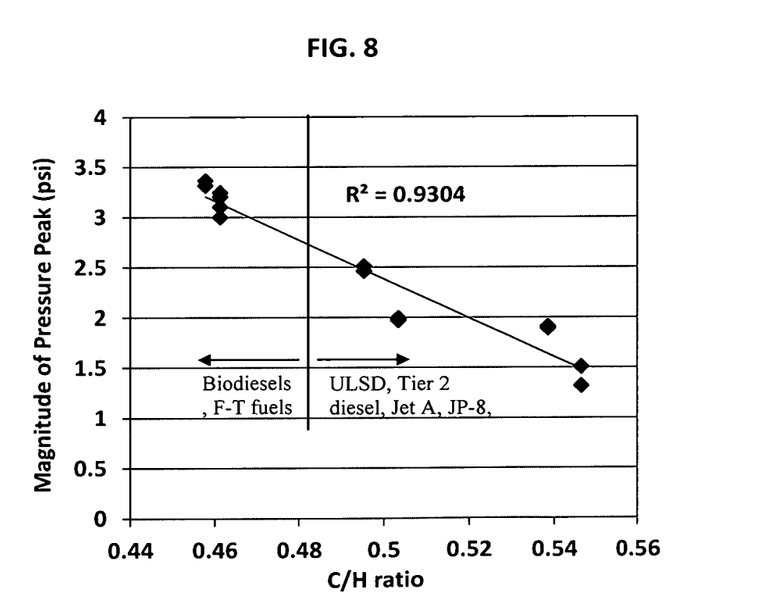
FIG. 8 depicts, for a set of liquid fuels, a calibration curve plotting magnitude of pressure peak as measured by this invention versus known C/H atomic ratio for each fuel.
Figure 9:
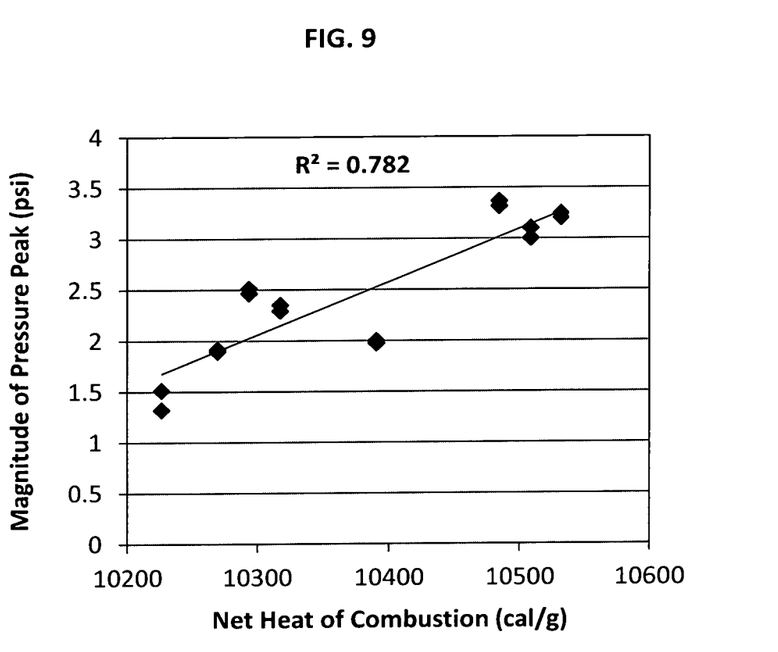
FIG. 9 depicts, for a set of liquid fuels, a calibration curve plotting magnitude of pressure peak as measured by this invention versus known net heat of combustion for each fuel.

FIGS. 7-9 present calibration curves plotting maximum magnitude of the pressure peak as measured in the process of this invention versus a physicochemical property of the fuel. In particular, FIG. 7 depicts a plot of the maximum magnitude of the pressure peak as a function of carbon content (wt. %) of each fuel. FIG. 8 depicts a plot of the maximum magnitude of the pressure peak as a function of C/H atomic ratio of each fuel. FIG. 9 depicts a plot of the maximum magnitude of the pressure peak as a function of heating value (cal/g, net heat of combustion) of each fuel.

Note that a clear cut-off line was observed in FIG. 8, wherein a C/H ratio of greater than 0.48 (>0.48) corresponded to conventional fuels and a C/H ratio of less than 0.48 (<0.48) corresponded to biodiesel and F-T fuels. Generally, biodiesels and F-T fuels have lower C/H ratios due to a higher content of long chain paraffinic hydrocarbons and a lower content of aromatics, as compared with conventional petroleum derived diesel and distillate fuels. Accordingly, the method of this invention is capable of distinguishing between conventional (petroleum-based fuels) and non-conventional (renewable biodiesels, F-T, and GTL fuels) in instances where a fuel's origin is unknown.

Example 6

The cetane sensor of this invention as described in the embodiment of Example 1 was evaluated for precision and accuracy of its results. Example 1 was repeated ten times using Jet A fuel with the cetane number results shown in Table 2.

TABLE 2

| Injection # | Cetane Number |
|---|---|
| 1 | 45.9 |
| 2 | 46.1 |
| 3 | 46.2 |
| 4 | 46.0 |
| 5 | 46.3 |
| 6 | 45.9 |
| 7 | 46.1 |
| 8 | 46.2 |
| 9 | 46.4 |
| 10 | 46.1 |

The highest cetane value obtained from this reproducibility study was 46.4 (Injection #9) and the lowest cetane value obtained was 45.9 (#1, #6), relating to a spread of 0.5. The average cetane number over ten measurements was 46.1+/−0.2. The cetane number of the sample of Jet A fuel as determined by the standard analytical method ASTM D-6890 was 45.3. The results indicate that the sensor and method of this invention provide precise and reproducible cetane number results with accuracy within 2 percent of the value determined by ASTM D-6890.

While the invention has been described in detail in connection with only a limited number of embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A sensor for a liquid fuel, comprising:
   (a) an ignition chamber having a ratio of surface-area-to-volume of greater than 4.7 per inch (1.9/cm);
   (b) a fuel dispenser disposed at or about midpoint of longest dimension of the chamber, the dispenser terminating within the chamber at a dispensing coordinate at or about midway along both vertical and horizontal transverse axes of the chamber;
   (c) an inlet line disposed at one end of the chamber;
   (d) an outlet line disposed at an opposite end of the chamber;
   (e) a heater connected to an exterior wall of the chamber;
   (f) at least one thermocouple connected to the chamber; and
   (g) a pressure transducer disposed in the inlet line or outlet line.

2. The sensor of claim 1 further comprising:
   (h) a data control analysis unit configured to (i) control a time of dispensing said liquid fuel into the chamber; (ii) record time and magnitude of a peak in pressure or temperature within the chamber after dispensing the liquid fuel; (iii) derive from the recordings of step (ii) a physicochemical property of the liquid fuel.

3. The sensor of claim 2 wherein the data control analysis unit is configured to calculate ignition delay as the difference between time of fuel dispensing and time at a point along the peak, and wherein ignition delay is correlated with cetane number of the liquid fuel.

4. The sensor of claim 2 wherein the data control analysis unit is configured to correlate the magnitude of the peak in pressure or temperature with carbon content, carbon-to-hydrogen atomic ratio, or heating value (net heat of combustion) of the liquid fuel.

5. The sensor of claim 1 wherein the ignition chamber has a surface-area-to-volume ratio greater than 4.7 per inch (1.9/cm) and less than 6.0 per inch (2.4/cm).

6. The sensor of claim 1 wherein the ignition chamber has an aspect ratio greater than 2.1:1 and less than 8.3:1.

7. The sensor of claim 1 wherein the fuel dispenser is configured to provide a dispensed volume of fuel ranging from 0.5 µl to 50 µl.

* * * * *